United States Patent
Veerabhadra Pratap et al.

(10) Patent No.: US 12,129,277 B2
(45) Date of Patent: *Oct. 29, 2024

(54) LINEAR SOLUTION PHASE ROUTES FOR WNT HEXAPEPTIDES

(71) Applicant: WNTRESEARCH AB, Malmö (SE)

(72) Inventors: Tadikonda Veerabhadra Pratap, Hyderabad (IN); Kamaraju Raghavendra Rao, Hyderabad (IN); Dennis Henriksen, Malmö (SE)

(73) Assignee: WNTRESEARCH AB, Malmö (SE)

( * ) Notice: Subject to any disclaimer, the term of this patent is extended or adjusted under 35 U.S.C. 154(b) by 629 days.

This patent is subject to a terminal disclaimer.

(21) Appl. No.: 17/299,745

(22) PCT Filed: Dec. 2, 2019

(86) PCT No.: PCT/EP2019/083309
§ 371 (c)(1),
(2) Date: Jun. 3, 2021

(87) PCT Pub. No.: WO2020/120198
PCT Pub. Date: Jun. 18, 2020

(65) Prior Publication Data
US 2022/0017568 A1 Jan. 20, 2022

(30) Foreign Application Priority Data

Dec. 14, 2018 (EP) .................... 18212658

(51) Int. Cl.
*C07K 1/06* (2006.01)
*C07K 14/475* (2006.01)

(52) U.S. Cl.
CPC ............ *C07K 1/063* (2013.01); *C07K 14/475* (2013.01)

(58) Field of Classification Search
None
See application file for complete search history.

(56) References Cited

U.S. PATENT DOCUMENTS 11,912,791 B2 * 2/2024 Henriksen .............. C07K 5/081

FOREIGN PATENT DOCUMENTS

| WO | WO 2010/019103 A1 | | 2/2010 |
| WO | WO 2010019103 | * | 2/2010 |
| WO | WO 2016/092378 A1 | | 6/2016 |
| WO | WO 2016092378 | * | 6/2016 |

OTHER PUBLICATIONS

Jenei Veronika et al: "A t-butyloxycarbonyl-modified Wnt5a-derived hexapeptide functions as a potent antagonist of Wnt5a-dependent melanoma cell invasion", Proceedings of the National Academy of Sciences of the United States of America, National Academy of Sciences, US, vol. 106, No. 46, Nov. 1, 2009 (Nov. 2009.*
Jenei et al., "A t-butyloxycarbonyl-modified Wnt5a-derived hexapeptide functions as a potent antagonist of Wnt5a-dependent melanoma cell invasion", PNAS, 2009, 106(46): 19473-19478.

* cited by examiner

*Primary Examiner* — Maury A Audet
(74) *Attorney, Agent, or Firm* — James S. Keddie; Bozicevic, Field & Francis LLP

(57) ABSTRACT

The present disclosure relates generally to the field of polypeptide synthesis, and more particularly, to a linear solution phase synthesis of the Wnt hexapeptide Foxy-5 and protected derivatives and peptide fragments thereof.

15 Claims, 5 Drawing Sheets
Specification includes a Sequence Listing.

SEQUENCE LISTING

<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: Formyl-methionine
<220> FEATURE:
<223> OTHER INFORMATION: Synthetic peptide

<400> SEQUENCE: 1

Met Asp Gly Cys Glu Leu
1               5

<210> SEQ ID NO 2
<211> LENGTH: 4
<212> TYPE: PRT
<213> ORGANISM: Artificial Sequence
<220> FEATURE:
<221> NAME/KEY: MOD_RES
<222> LOCATION: 1
<223> OTHER INFORMATION: (Fluorenylmethoxycarbonyl)-glycine

```
<220> FEATURE:
<223> OTHER INFORMATION: Synthetic peptide
<220> FEATURE:
<221> NAME/KEY: MOD_RES
<222> LOCATION: 2
<223> OTHER INFORMATION: Trityl-cystein
<220> FEATURE:
<221> NAME/KEY: MOD_RES
<222> LOCATION: 3
<223> OTHER INFORMATION: Glutamic acid tert-butylester
<220> FEATURE:
<221> NAME/KEY: MOD_RES
<222> LOCATION: 4
<223> OTHER INFORMATION: Leucine tert-butylester

<400> SEQUENCE: 2

Gly Cys Glu Leu
1

<210> SEQ ID NO 3
<211> LENGTH: 5
<212> TYPE: PRT
<213> ORGANISM: Artificial Sequence
<220> FEATURE:
<221> NAME/KEY: MOD_RES
<222> LOCATION: 1
<223> OTHER INFORMATION: (Fluorenylmethoxycarbonyl)-aspartic acid
      tert-butyl ester
<220> FEATURE:
<223> OTHER INFORMATION: Synthetic peptide
<220> FEATURE:
<221> NAME/KEY: MOD_RES
<222> LOCATION: 3
<223> OTHER INFORMATION: Trityl-cystein
<220> FEATURE:
<221> NAME/KEY: MOD_RES
<222> LOCATION: 4
<223> OTHER INFORMATION: Glutamic acid tert-butylester
<220> FEATURE:
<221> NAME/KEY: MOD_RES
<222> LOCATION: 5
<223> OTHER INFORMATION: Leucine tert-butylester

<400> SEQUENCE: 3

Asp Gly Cys Glu Leu
1               5

<210> SEQ ID NO 4
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: (Fluorenylmethoxycarbonyl)-methionine
<220> FEATURE:
<223> OTHER INFORMATION: Synthetic peptide
<220> FEATURE:
<221> NAME/KEY: MOD_RES
<222> LOCATION: 2
<223> OTHER INFORMATION: Aspartic acid tert-butylester
<220> FEATURE:
<221> NAME/KEY: MOD_RES
<222> LOCATION: 4
<223> OTHER INFORMATION: Trityl-cystein
<220> FEATURE:
<221> NAME/KEY: MOD_RES
<222> LOCATION: 5
<223> OTHER INFORMATION: Glutamic acid tert-butylester
<220> FEATURE:
<221> NAME/KEY: MOD_RES
<222> LOCATION: 6
<223> OTHER INFORMATION: Leucine tert-butylester

<400> SEQUENCE: 4
```

```
Met Asp Gly Cys Glu Leu
1               5

<210> SEQ ID NO 5
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: Formyl-methionine
<220> FEATURE:
<223> OTHER INFORMATION: Synthetic peptide
<220> FEATURE:
<221> NAME/KEY: MOD_RES
<222> LOCATION: 2
<223> OTHER INFORMATION: Aspartic acid tert-butylester
<220> FEATURE:
<221> NAME/KEY: MOD_RES
<222> LOCATION: 4
<223> OTHER INFORMATION: Trityl-cystein
<220> FEATURE:
<221> NAME/KEY: MOD_RES
<222> LOCATION: 5
<223> OTHER INFORMATION: Glutamic acid tert-butylester
<220> FEATURE:
<221> NAME/KEY: MOD_RES
<222> LOCATION: 6
<223> OTHER INFORMATION: Leucine tert-butylester

<400> SEQUENCE: 5

Met Asp Gly Cys Glu Leu
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Gly Cys Glu Leu
1

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Asp Gly Cys Glu Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Met Asp Gly Cys Glu Leu
1               5
```

LINEAR SOLUTION PHASE ROUTES FOR WNT HEXAPEPTIDES

CROSS-REFERENCE TO RELATED APPLICATIONS

This application is a § 371 national phase of International Application No. PCT/EP2019/083309, filed on Dec. 2, 2019, which claims the benefit of European Application No. 18212658.1, filed on Dec. 14, 2018, which applications are incorporated by reference herein.

FIELD OF THE INVENTION

The present disclosure relates generally to the field of polypeptide synthesis, and more particularly, to a linear solution phase approach towards Wnt hexapeptide Foxy-5. The present disclosure further relates to the solution phase synthesis of novel Foxy-5 tri-, tetra- and pentapeptide fragments.

BACKGROUND OF THE INVENTION

Foxy-5 is a formylated, WNT5A-derived hexapeptide and WNT5A mimetic with potential anti-metastatic activity currently in development as a drug candidate for the prevention of tumor spread in several common forms of cancer.

Foxy-5 has the amino acid sequence For-Met-Asp-Gly-Cys-Glu-Leu-OH (SEQ_NO 1, FIG. 1.)

Upon intravenous administration, Foxy-5 binds to and activates WNT5A receptors, predominantly of the Frizzled family, which activates WNT5A-mediated signaling.

Foxy-5 is intended to compensate for the deficiency of protein WNT5A in tumor tissue noted in patients with colon cancer, in order to reduce the risk of metastasis. A sub-analysis from a recent retrospective study of patients with colorectal cancer in stage III, shows that the proportion of patients with low expression of WNT5A is significantly higher than that observed in previous studies in patients with stage II colorectal cancer (CRC). Patients with CRC stage III tumors differ from stage II mainly by the presence of tumor cells in lymph nodes adjacent to the primary tumor, thereby being more aggressive and faster progressing. A low level of WNT5A has been observed in close to 70 percent of patients in stage III, compared with approximately 45 percent of patients with less advanced tumor stages. This supports the hypothesis that the WNT5A level significantly influences the course of disease.

Based on a completed Phase 1b study with Foxy-5 aimed at documenting the drug candidate's safety profile, pharmacokinetics and dose determination for Phase 2, Foxy-5 is now posed for a Phase 2 clinical trial study, where treatment in colon cancer patients will be initiated at the time of diagnosis, before surgery has been conducted. The treatment is intended to last for a maximum of 12 weeks, or until the initiation of chemotherapy.

Foxy-5 and a method for its preparation are described in International Pat. Publication No. WO06130082 A1. The active pharmaceutical ingredient (API) for the preclinical and clinical studies conducted so far has been produced by classical solid phase peptide synthesis (SPPS), whereby Foxy-5 is produced by a linear 1+1+1+1+1+1 route, see FIG. 2.

The sequence For-Met-Asp-Gly-Cys-Glu-Leu-OH is thus assembled on a 2-chlorotrityl resin carrying the C-terminal amino acid Leu using the Fmoc-strategy (Fmoc=fluorenylmethyloxycarbonyl). Synthesis is performed in an SPPS reactor and consists of alternating coupling, acetylation, and N-α-deprotection procedures. The coupling is performed in DMF (N,N-dimethylformamide) or DMF/DCM (dichloromethane) as solvent. It consists of coupling the N-α-protected amino acid derivative to the preceding amino acid in the presence of an activating reagent and a base, if necessary. Formic acid is coupled as an active ester without activating agents.

If the coupling is not complete, it can be continued or the procedure can be repeated. In order to avoid the formation of deletion sequences as by-products, a systematic acetylation procedure (capping) is performed after the coupling step or, if recoupling is performed after the recoupling steps, using DMF, acetic anhydride, and pyridine.

Acetylation is followed by an N-α-deprotection procedure which consists of washing the resin with DMF, cleaving the Fmoc-group with piperidine in DMF, and subsequent washings with DMF. In case of incomplete cleavage, the N-α-deprotection procedure as described above can be repeated. For each single step, the solvents and/or reagents are added, and the reaction mixture is stirred and then filtered to remove solvents and/or reagents from the resin.

Coupling, acetylation, and N-α-deprotection procedures are repeated until the resin carries the complete peptide sequence For-Met-Asp-Gly-Cys-Glu-Leu-OH. After the final coupling of the formic acid active ester, no acetylation is performed. The SPPS is completed by washing the peptide resin with DMF and IPA and subsequent drying under reduced pressure.

Cleavage of the peptide from the resin and concomitant cleavage of the side-chain protecting groups is accomplished by treatment of the peptide resin with TFA in the presence of suitable scavengers (e.g. water and EDT). Subsequently, the crude peptide obtained is purified by two-dimensional preparative HPLC on a reversed phase column with ACN gradient elution (formic acid and acetic acid systems).

Pooled fractions with adequate purity are lyophilized. The lyophilizate is analyzed by HPLC and optionally repurified by two-dimensional preparative HPLC as outlined above in case of non-compliance with the set criteria for purity.

The SPPS approach outlined above has generated sufficient material for the preclinical and early clinical research, but for further clinical studies and eventual commercial purposes, a synthesis better suited for large scale synthesis is required, by which the cost of goods can be reduced and larger batches of Foxy-5 can be made available.

There is thus a need for a reliable route of synthesis which can provide Foxy-5 in multi-kg scale, both for further clinical trial supply and eventual commercial purposes.

ABBREVIATIONS

Figure 1:
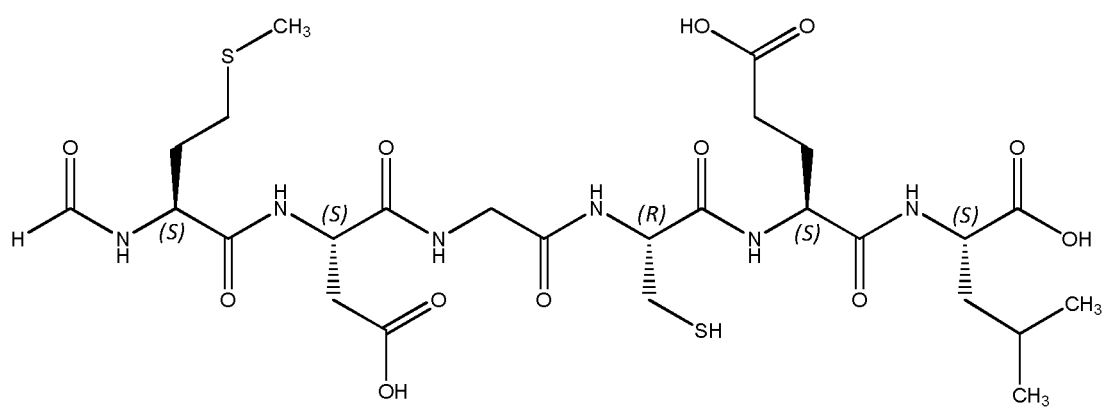
FIG. 1 shows the chemical structure of Foxy-5. Foxy-5 is a linear peptide consisting of six amino acids with a formylated N-terminus. All optically active amino acid residues are in the L-configuration. The molecular formula of Foxy-5 is $C_{26}H_{42}N_6O_{12}S_2$, and the molecular mass is 694.8 g/mol (average mass).
Figure 2:
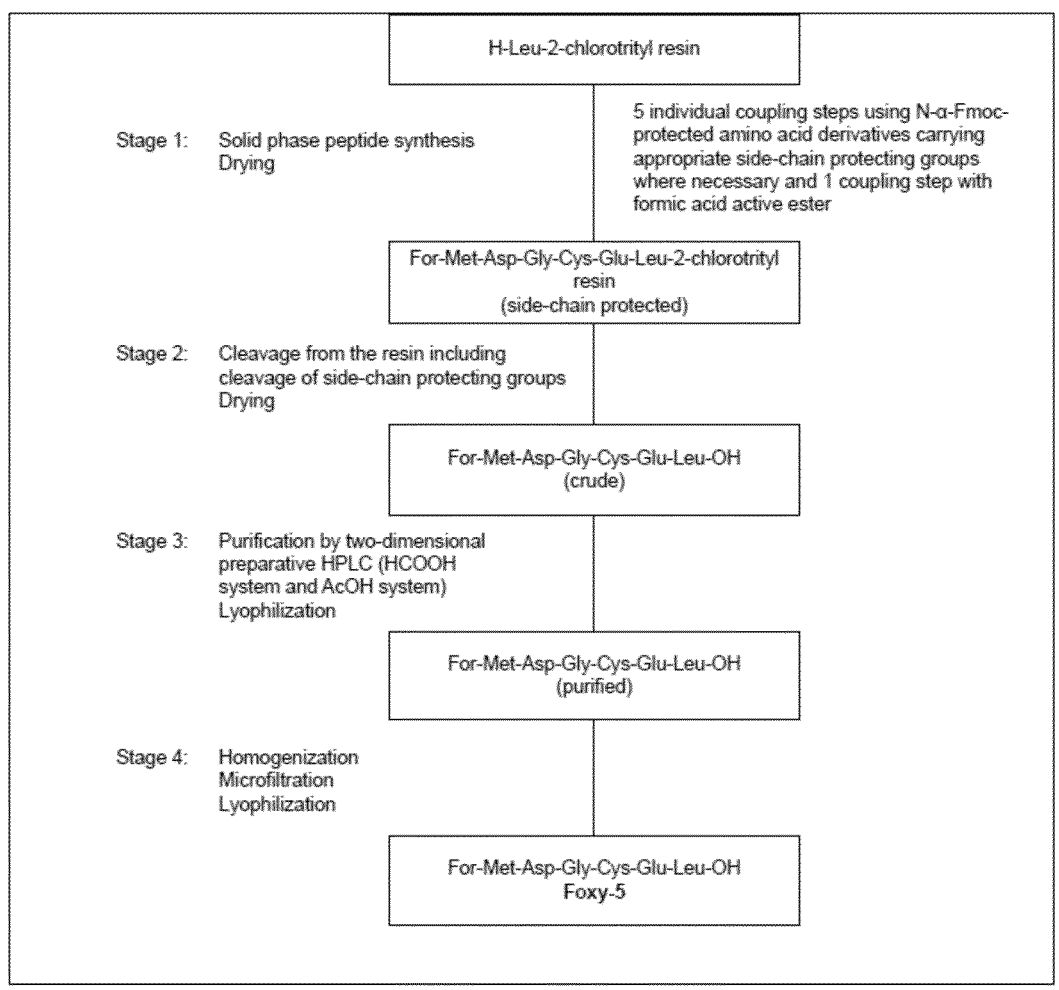
FIG. 2 shows the synthetic scheme for the SPPS route to Foxy-5.
Figure 3:
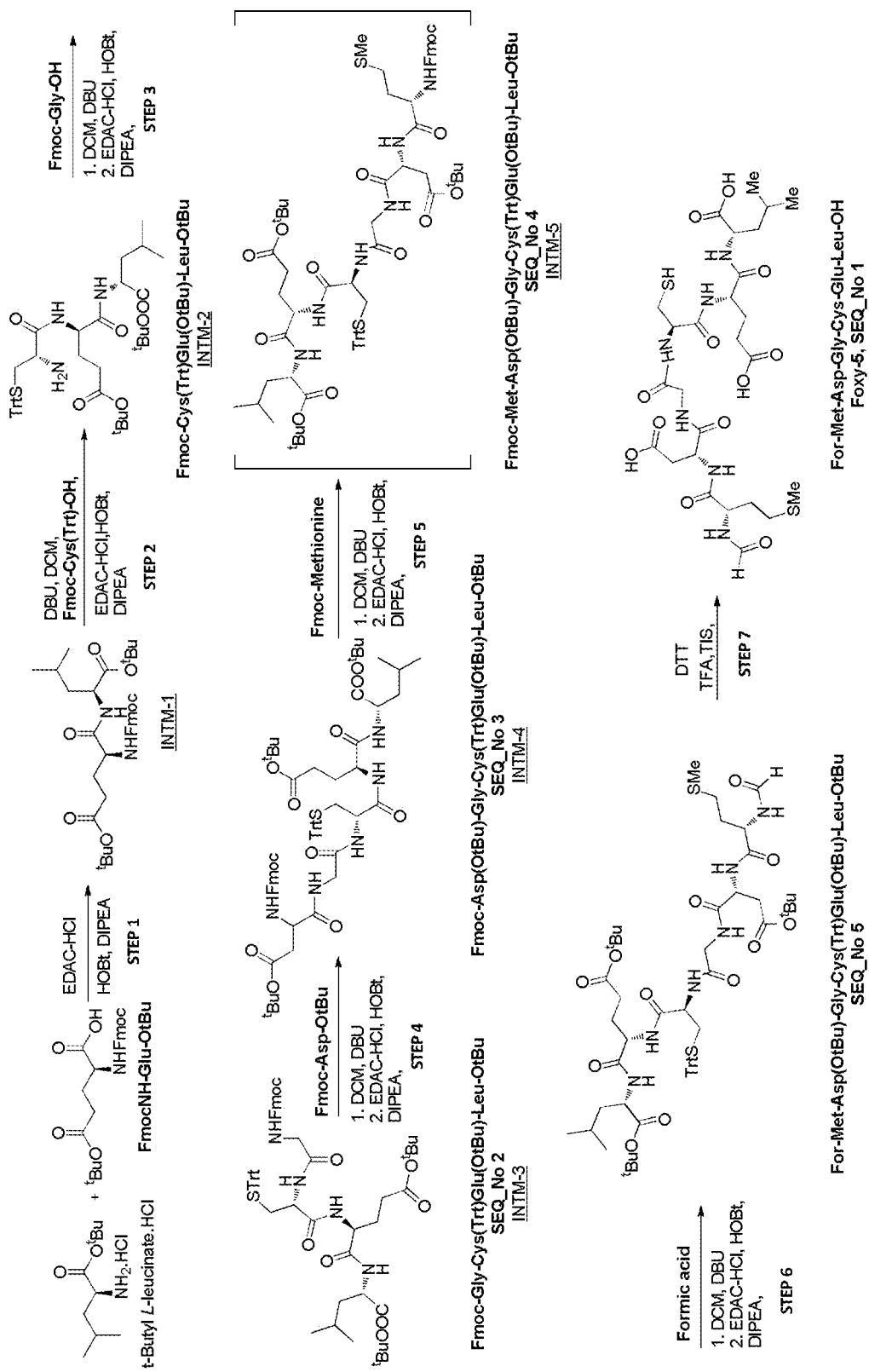
FIG. 3 illustrates a linear 1+1+1+1+1+1 strategy for the formation of Foxy-5.

Fmoc=Fluorenylmethoxycarbonyl
Tfa=trifluoroacetyl
Tsoc=4-toluenesulfonylethyloxycarbonyl
Mesoc=methylsulfonylethyloxycarbonyl
Peoc=2-(triphenylphosphono) ethyloxycarbonyl
Cyoc=2-cyano-t-butyloxycarbonyl and
Pht=phthalyl
Nsc=2-(4-nitrophenylsulfonyl) ethoxycarbonyl
Boc=tert-Butyloxycarbonyl
For=Formyl
Trt=Triphenyl methyl (Trityl)
tBu=tert-Butyl
THF=Tetrahydrofuran
DIPE=Di-isopropylether
DMF=N, N-Dimethylformamide
TFA=Trifluoroacetic acid
TIS=Triisopropylsilane
HOBt=1-Hydroxybenzotriazole
DCM=Dichloromethane
EDAC, HCl=1-Ethyl-3-(3'-dimethylaminopropyl)carbodiimide, HCl
DIPEA=Diisopropylamine
DBU=1,8-Diazabicyclo[5.4.0]undec-7-ene Amino Acid Abbreviations Met=Methionine
Asp=Asparagine
Gly=Glycine
Cys=Cysteine
Glu=Glutamic acid
Leu=Leucine
Foxy-5=For-Met-Asp-Gly-Cys-Glu-Leu

SUMMARY OF THE INVENTION

The instant disclosure provides a linear solution-phase method for preparing the formylated hexapeptide known as "Foxy-5" (i.e. For-Met-Asp-Gly-Cys-Glu-Leu-OH (SEQ_NO 1)), and also various tri-, tetra-, penta- and hexapeptide fragments thereof, including protected derivatives thereof. The method provided herein possesses many advantages over traditional solid phase syntheses, including but not limited to, low raw materials costs, ease of purification of process intermediates, ease of fragment assembly, high chiral purity, and adaptability to commercial scale-up, to be described in greater detail below.

It is thus a primary objective of the present invention to provide a scalable route of synthesis for Foxy-5. It is a further objective to identify and characterize suitable Key intermediates for said scalable route of synthesis for the purpose of later GMP (Good Manufacturing Practice) manufacture of the drug substance.

In view of the cost of goods and cumbersome scalability normally associated with solid phase chemistry, the focus has been on developing solution phase chemical routes. The instant disclosure provides a linear (1+1+1+1+1+1) solution phase approach to the preparation of Foxy-5, or intermediates and precursors thereof.

In contrast to traditional, convergent solution phase approaches for hexapeptides whereby di- or tripeptides are individually produced followed by coupling, the inventors have surprisingly found that a linear route, whereby the peptide sequence of Foxy-5 is assembled by sequential solution phase coupling of protected derivatives of amino acids Met, Asp, Gly, Cys, Glu and Leu, can be made to work very efficiently.

The central part of the invention lies in the introduction of the formyl (For) group on the methionine N-terminus. As will be discussed later in this application, this particular chemical step has been the most difficult to achieve in good yield and high chemical and optical purity.

The inventors have now found that a hexapeptide derivative of the formula PG-Met-Asp(OtBu)-Gly-Cys(Trt)-Glu(OtBu)-Leu-OR may serve excellently as a Foxy-5 precursor, and preferably when R is selected from $C_1$-$C_6$ alkyl, such as methyl or t-butyl, and PG is a base-sensitive protecting group for nitrogen, i.e. a protecting group which is stable under acidic conditions but which can be cleaved off the peptide under alkaline/basic conditions. In the context of the present invention, protecting groups such as Fmoc, Tfa, Tsoc, Mesoc, Peoc, Cyoc or Nsc are suitable, preferably Fmoc.

In a first aspect the present invention therefore provides a hexapeptide derivative of the formula PG-Met-Asp(OtBu)-Gly-Cys(Trt)-Glu(OtBu)-Leu-OR, wherein R is selected from $C_1$-$C_6$ alkyl, such as methyl or t-butyl, and PG is a base-sensitive protecting group such as Fmoc, Tfa, Tsoc, Mesoc, Peoc, Cyoc or Nsc.

The hexapeptide derivative of the first aspect may be converted to the desired hexapeptide Foxy-5 by N-deprotection, followed by coupling with formic acid, and finally a global deprotection of the remaining protecting groups.

In a second aspect, the present invention thus provides a method for preparing hexapeptide Foxy-5 (SEQ_NO 1), the method comprising:
 a. Providing a hexapeptide derivative according to the first aspect,
 b. Removing the PG protecting group from said hexapeptide derivative,
 c. Coupling the obtained product of step b) with Formic acid or an active ester thereof to produce a protected Foxy-5 derivative, For-Met-Asp(OtBu)-Gly-Cys(Trt)-Glu(OtBu)-Leu-OR,
 d. Globally deprotecting the obtained protected Foxy-5 derivative of step c) to produce Foxy-5 in crude form,
 e. Optionally performing additional purification steps, and
 f. Optionally precipitating the formed Foxy-5 hexapeptide as an alkaline or acidic salt in solid form,
wherein R is selected from $C_1$-$C_6$ alkyl, such as methyl or t-butyl, and PG is a base-sensitive protecting group such as Fmoc, Tfa, Tsoc, Mesoc, Peoc, Cyoc or Nsc.

The hexapeptide derivative of the first aspect may be prepared by any convenient method such as solid phase synthesis or solution phase methods, and most conveniently by the method developed by the present inventors presented hereinbelow.

In a third aspect the present invention provides a method for the preparation of the hexapeptide derivative according to the first aspect comprising the following steps:
 a. Providing a protected L-leucine derivative PG-Leu-OR,
 b. Removing the protecting group PG from said protected L-leucine derivative followed by coupling with PG-Glu-OtBu to produce a protected dipeptide PG-Glu(OtBu)-Leu-OR,
 c. Removing the protecting group PG from said said protected dipeptide followed by coupling with PG-Cys(Trt)-OH to produce a protected tripeptide PG-Cys(Trt)-Glu(OtBu)-Leu-OR, d. Removing the protecting group PG from said protected tripeptide followed by coupling with PG-Gly-OH to produce a protected tetrapeptide PG-Gly-Cys(Trt)-Glu(OtBu)-Leu-OR, e. Removing the protecting group PG from said protected tetrapeptide under basic conditions, followed by removing excess base, to produce a deblocked tetrapeptide H-Gly-Cys(Trt)-Glu(OtBu)-Leu-OR, f. Coupling said deblocked tetrapeptide with PG-Asp(OtBu) under basic conditions, followed by removing excess base, to produce a protected pentapeptide PG-Asp(OtBu)-Gly-Cys(Trt)-Glu(OtBu)-Leu-OR, g. Removing the protecting group PG from said deblocked pentapeptide followed by coupling with formic acid or an active ester thereof to produce the protected hexapeptide PG-Met-Asp(OtBu)-Gly-Cys(Trt)-Glu(OtBu)-Leu-OR, wherein R is selected from $C_1$-$C_6$ alkyl, such as methyl or t-butyl and PG is a base-sensitive protecting group such as Fmoc, Tfa, Tsoc, Mesoc, Peoc, Cyoc or Nsc.

The above aspects of the present invention, including preferred embodiments thereof, will be discussed further in the following.

In a fourth aspect of the present invention there is provided a method of production for the hexapeptide Foxy-5 in protected form, based on the sequential coupling of the tripeptide intermediate INTM-2, Fmoc-Cys(Trt)Glu(OtBu)-Leu-OtBu, with protected derivatives of amino acids Gly, Asp and Met, followed by N-deprotection and coupling with formic acid.

In a fifth aspect of the present invention there is provided a method of production for the hexapeptide Foxy-5 in protected form, based on the sequential coupling of the tetrapeptide intermediate INTM-3, Fmoc-Gly-Cys(Trt)Glu(OtBu)-Leu-OtBu, with protected derivatives of amino acids Asp and Met, followed by N-deprotection and coupling with formic acid.

In further aspects of the present invention, the following peptides are provided:

```
Fmoc-Cys(Trt)Glu(OtBu)-Leu-OtBu (SEQ_NO 2)
Fmoc-Gly-Cys(Trt)Glu(OtBu)-Leu-OtBu (SEQ_NO 3)
Fmoc-Asp(OtBu)-Gly-Cys(Trt)Glu(OtBu)-

Leu-OtBu (SEQ_NO 4)
Fmoc-Met-Asp(OtBu)-Gly-Cys(Trt)Glu(OtBu)-

Leu-OtBu (SEQ_NO 5)
For-Met-Asp(OtBu)-Gly-Cys(Trt)Glu(OtBu)-

Leu-OtBu

Cys-Glu-Leu (SEQ_NO 6)
Gly-Cys-Glu-Leu (SEQ_NO 7)
Asp-Gly-Cys-Glu-Leu (SEQ_NO 8)
Met-Asp-Gly-Cys-Glu-Leu
```

DETAILED DESCRIPTION

As mentioned in the summary hereinabove a linear solution phase approach for assembling the Foxy-5 hexapeptide sequence has been devised, which will be discussed in more detail in the following.

The general approach has been to protect all amino acids as O-$^t$Bu, N-Fmoc derivatives. Moreover, the target has been a synthesis which is as "telescoped" as possible, thereby avoiding time consuming and costly isolation of intermediates. Preferably, each step in the sequence should be possible to carry out without product isolation, just allowing for minor purification steps such as an aqueous workup of organic solvent solutions and silica plug treatments ("flash chromatography") to remove excess base, for example.

The linear synthesis starts by the preparation in two telescoped steps (STEP 1+2) of the tripeptide INTM-2, Fmoc-Cys(Trt)Glu(OtBu)-Leu-OtBu, by coupling of t-Butyl L-leucinate, HCl with Fmoc-Glu(OtBu) in dichloromethane (DCM) as a reaction solvent. The reaction mixture is worked up with water and brine, and the DCM solution is used directly in STEP 2 without isolation of the intermediary dipeptide, INTM-1, Fmoc-Glu(OtBu)Leu-OtBu.

In STEP 2 the DCM solution of INTM-1 is reacted with Fmoc-Cys(Trt)-OH to furnish the desired tripeptide INTM-2, Fmoc-Cys(Trt)Glu(OtBu)-Leu-OtBu. The reactions proceed well, and repeatedly give combined yields of ~68% over two steps. INTM-2 can be purified by chromatography over silica gel (100-200) as a white color solid. The obtained DCM solution can also be carried forward as such and used directly in STEP 3, coupling with Fmoc-Gly-OH.

In STEP 3, INTM-2 is Fmoc-deprotected with DBU and coupled with Fmoc-Gly-OH in DCM to afford the tetrapeptide INTM-3, Fmoc-Gly-Cys(Trt)Glu(OtBu)-Leu-OtBu. After completion of reaction, the DCM layer is washed with water and brine. The final organic layer is then concentrated from 50 volumes to 10-15 volumes, and carried forward as such to the next stage (STEP 4) without isolation.

Figure 4:
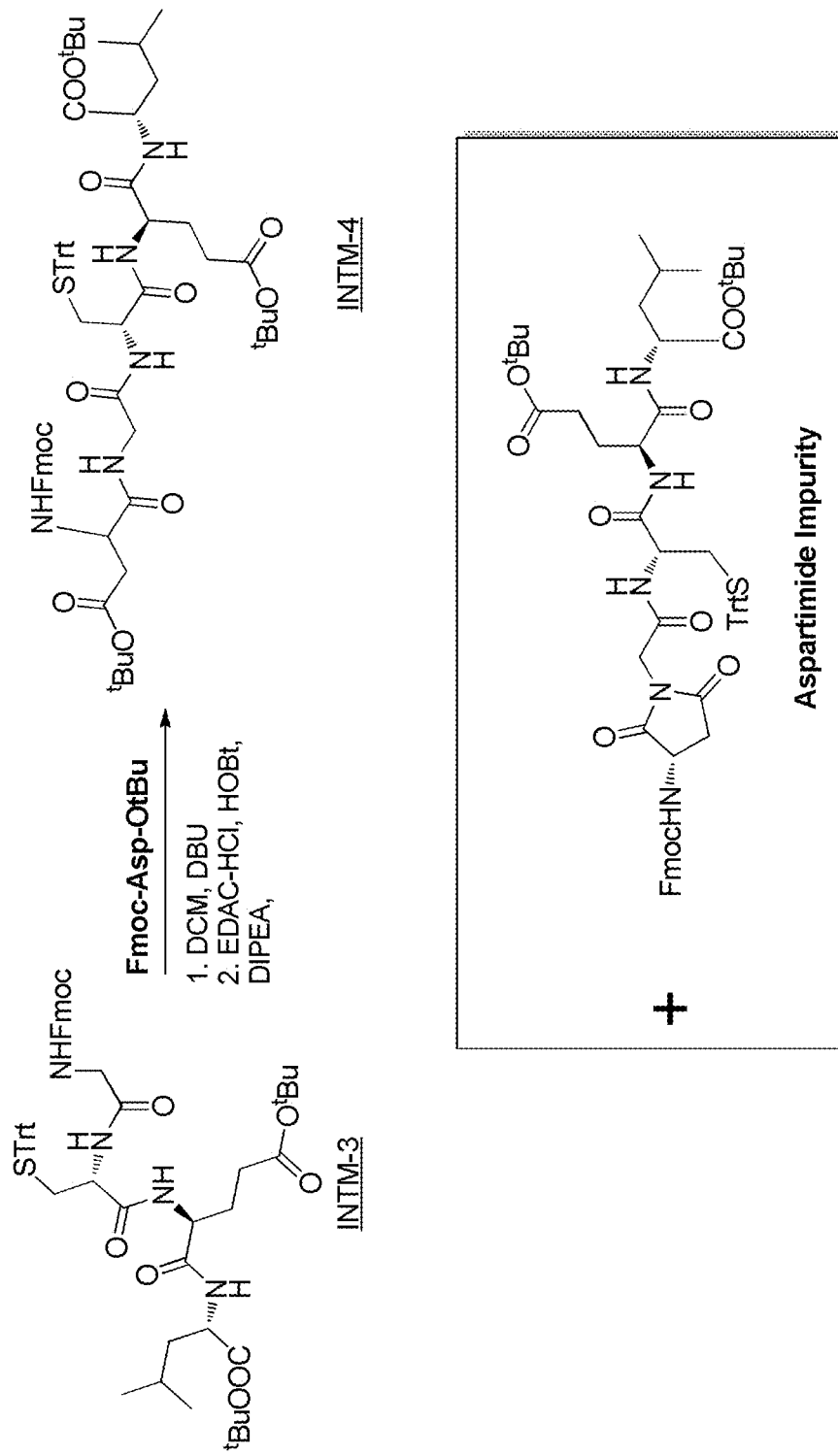
FIG. 4 illustrates the formation of the "aspartimide impurity".

In STEP 4, the DCM solution of INTM-3 is first treated with DBU to effect deprotection of the Fmoc group. After deblocking, the reaction mass is passed through a silica plug column to remove the DBU before coupling the tetrapeptide with Fmoc-Asp-OtBu in the presence of EDC.HCl, HOBt Hydrate and DIPEA. After completion of the reaction, the reaction mass is again passed through a silica plug column to remove the DIPEA still present. The removal as described of DBU and DIPEA is essential in order to suppress the formation of an undesired aspartimide impurity, see FIG. 4. Performed this way, yields of ~60% of INTM-4, Fmoc-Asp(OtBu)-Gly-Cys(Trt)-Glu(OtBu)-Leu-OtBu, were observed over two steps (STEP 3+4) on 100-160 gr scale. In the presence of DBU, the observed yield was only about 25%.

In STEP 5, INTM-4 is Fmoc-deprotected with DBU in DCM as a solvent and coupled with Fmoc-Methionine to furnish intermediate INTM-5 Fmoc-Met-Asp(OtBu)-Gly-Cys(Trt)-Glu(OtBu)-Leu-OtBu (SEQ_NO 4) in crude form. Purification is performed by column chromatography using DCM/THF as eluent. The purified product is slurried in DIPE to afford a white colored solid.

Figure 5:
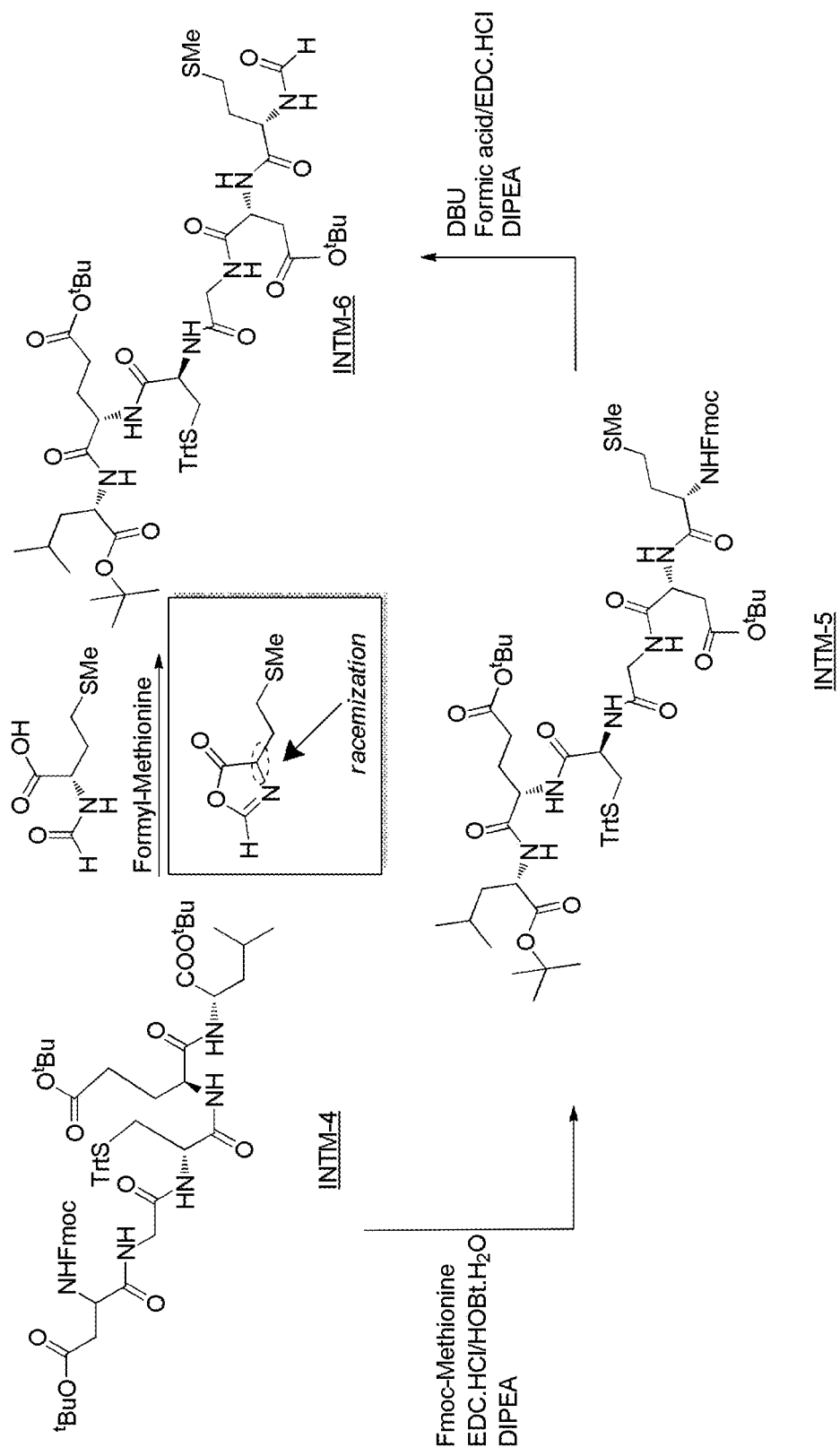
FIG. 5 illustrates the role of the formyl group in an observed epimerization reaction.

Initially, it was attempted to perform the coupling of INTM-4 directly with N-formyl-methionine (For-Met-OH) to produce hexapeptide INTM-6, but this synthetic strategy was found to lead to partial epimerization in the final product because For-Met-OH cyclizes reversibly under the reaction conditions to produce an oxazolidone, which causes the For-Met-OH reagent to racemize. See FIG. 5. Instead, using Fmoc-Methionine followed by DBU-deprotection of the Fmoc group and coupling with formic acid, or an active ester thereof, leads to desired intermediate hexapeptide INTM-6. Global deprotection hereof (of Trt and O-tBu groups) provides Foxy-5 in crude form, which may be purified further, e.g. by chromatography, and/or precipitated as a solid, such as as an acidic or alkaline addition salt.

In a first aspect the present invention therefore provides a hexapeptide derivative of the formula PG-Met-Asp(OtBu)-Gly-Cys(Trt)-Glu(OtBu)-Leu-OR, wherein R is selected from $C_1$-$C_6$ alkyl, such as methyl or t-butyl, and PG is a base-sensitive protecting group such as Fmoc, Tfa, Tsoc, Mesoc, Peoc, Cyoc or Nsc.

In an embodiment of the first aspect, PG is Fmoc.

In another embodiment of the first aspect there is provided a hexapeptide derivative of the formula Fmoc-Met-Asp(OtBu)-Gly-Cys(Trt)-Glu(OtBu)-Leu-OR, wherein R is selected from $C_1$-$C_6$ alkyl, such as methyl or t-butyl.

In a preferred embodiment of the first aspect, the hexapeptide derivative has the formula

```
                                              (SEQ_NO 4)
      Fmoc-Met-Asp(OtBu)-Gly-Cys(Trt)-

Glu(OtBuLeu-OtBu.
```

In a second aspect, the present invention provides a method for preparing the hexapeptide Foxy-5 (SEQ_NO 1), the method comprising:
 a. Providing a hexapeptide derivative according to the first aspect,
 b. Removing the PG protecting group from said hexapeptide derivative,
 c. Coupling the obtained product of step b) with Formic acid or an active ester thereof to produce a protected Foxy-5 derivative, For-Met-Asp(OtBu)-Gly-Cys(Trt)-Glu(OtBu)-Leu-OR,
 d. Globally deprotecting the obtained protected Foxy-5 derivative of step c) to produce Foxy-5 in crude form,
 e. Optionally performing additional purification steps, and
 f. Optionally precipitating the formed Foxy-5 hexapeptide as an alkaline or acidic salt in solid form,
wherein R is selected from $C_1$-$C_6$ alkyl, such as methyl or t-butyl, and PG is a base-sensitive protecting group such as Fmoc, Tfa, Tsoc, Mesoc, Peoc, Cyoc or Nsc.

In an embodiment of the second aspect, PG is Fmoc.

In another embodiment of the second aspect, the alkyl group R is t-Butyl.

In another embodiment of the second aspect the coupling with Formic acid or an active ester thereof takes place in solution.

In another embodiment of the second aspect the obtained crude Foxy-5 is purified by chromatography, such as reverse phase chromatography In another embodiment of the second aspect the obtained Foxy-5 is precipitated as an alkaline or acidic salt in solid form.

In another embodiment of the second aspect the obtained Foxy-5 is isolated as a crystalline alkaline or acidic salt.

In a third aspect the present invention provides a method for the preparation of the hexapeptide derivative according to the first aspect comprising the following steps:
 a. Providing a protected L-leucine derivative PG-Leu-OR,
 b. Removing the protecting group PG from said protected L-leucine derivative by coupling with PG-Glu-OtBu to produce a protected dipeptide PG-Glu(OtBu)-Leu-OR,
 c. Removing the protecting group PG from said said protected dipeptide followed by coupling with PG-Cys(Trt)-OH to produce a protected tripeptide PG-Cys(Trt)-Glu(OtBu)-Leu-OR,
 d. Removing the protecting group PG from said protected tripeptide followed by coupling with PG-Gly-OH to produce a protected tetrapeptide PG-Gly-Cys(Trt)-Glu(OtBu)-Leu-OR,
 e. Removing the protecting group PG from said protected tetrapeptide under basic conditions, followed by removing excess base, to produce a deblocked tetrapeptide H-Gly-Cys(Trt)-Glu(OtBu)-Leu-OR,
 f. Coupling said deblocked tetrapeptide with PG-Asp(OtBu) under basic conditions, followed by removing excess base, to produce a protected pentapeptide PG-Asp(OtBu)-Gly-Cys(Trt)-Glu(OtBu)-Leu-OR,
 g. Removing the protecting group PG from said deblocked pentapeptide followed by coupling with formic acid or an active ester thereof to produce the protected hexapeptide PG-Met-Asp(OtBu)-Gly-Cys(Trt)-Glu(OtBu)-Leu-OR,
  wherein R is selected from $C_1$-$C_6$ alkyl, such as methyl or t-butyl and PG is a base-sensitive protecting group such as Fmoc, Tfa, Tsoc, Mesoc, Peoc, Cyoc or Nsc,
wherein R is selected from $C_1$-$C_6$ alkyl, such as methyl or t-butyl, and PG is a base-sensitive protecting group such as Fmoc, Tfa, Tsoc, Mesoc, Peoc, Cyoc or Nsc.

In an embodiment of the third aspect, PG is Fmoc.

In an embodiment of the third aspect, all steps b)-g) are performed in solution.

In a further embodiment, the hexapeptide derivative according to the first aspect is obtainable by the method according to the third aspect.

In a preferred embodiment of the third aspect, the base-sensitive protecting group PG is Fmoc, and the alkyl group R is t-Butyl.

In another embodiment of the third aspect, at least two consecutive coupling steps, such as two, three or four steps, are performed without product isolation.

The present invention thus in a preferred embodiment provides the following sequence of steps for the production of the hexapeptide Foxy-5 in crude form:
 1. coupling of Leu-OtBu with Fmoc-Glu-OtBu to produce the dipeptide INTM-1, Fmoc-Glu(OtBu)-Leu-OtBu, followed by
 2. coupling hereof with Fmoc-Cys(Trt)-OH to produce the tripeptide INTM-2, Fmoc-Cys(Trt)Glu(OtBu)-Leu-OtBu, followed by
 3. coupling hereof with Fmoc-Gly-OH to afford protected tetrapeptide INTM-3, Fmoc-Gly-Cys(Trt)Glu(OtBu)-Leu-OtBu (SEQ_NO 2), followed by
 4. coupling hereof with Fmoc-Asp-OtBu to afford protected pentapeptide INTM-4, Fmoc-Asp(OtBu)-Gly-Cys(Trt)Glu(OtBu)-Leu-OtBu (SEQ_NO 3), followed by
 5. coupling with Fmoc-Met to afford protected hexapeptide INTM-5 Fmoc-Met-Asp(OtBu)-Gly-Cys(Trt)Glu(OtBu)-Leu-OtBu (SEQ_NO 4), followed by
 6. reaction hereof with formic acid to afford Foxy-5 in protected form, i.e. INTM-6, For-Met-Asp(OtBu)-Gly-Cys(Trt)Glu(OtBu)-Leu-OtBu (SEQ_NO 5), followed by
 7. global deprotection of t-Bu and Trt groups to produce Foxy-5, i.e. For-Met-Asp-Gly-Cys-Glu-Leu-OH (SEQ_NO 1), in crude form.

In a fourth aspect there is provided a method of production for the hexapeptide Foxy-5 in protected form, i.e.

INTM-6 For-Met-Asp(OtBu)-Gly-Cys(Trt)Glu(OtBu)-Leu-OtBu (SEQ_NO 5), based on the sequential coupling of the novel tripeptide intermediate INTM-2, Fmoc-Cys(Trt)Glu(OtBu)-Leu-OtBu with protected derivatives of amino acids Gly, Asp and Met, followed by N-deprotection and coupling with formic acid.

In an embodiment, the intermediate INTM-2, Fmoc-Cys(Trt)Glu(OtBu)-Leu-OtBu is produced by solid phase synthesis. In a preferred embodiment, said intermediate INTM-2 is produced by solution phase synthesis.

In a fifth aspect there is provided a method of production for the hexapeptide Foxy-5 in protected form, i.e. INTM-6 For-Met-Asp(OtBu)-Gly-Cys(Trt)Glu(OtBu)-Leu-OtBu (SEQ_NO 5) based on the sequential coupling of the novel tetrapeptide intermediate INTM-3, Fmoc-Gly-Cys(Trt)Glu(OtBu)-Leu-OtBu with protected derivatives of amino acids Asp and Met, followed by N-deprotection and coupling with formic acid.

In an embodiment, the intermediate INTM-3, Fmoc-Gly-Cys(Trt)Glu(OtBu)-Leu-OtBu is produced by solid phase synthesis. In a preferred embodiment, said intermediate INTM-3 is produced by solution phase synthesis.

In further aspects of the present invention, the following peptides are provided:

```
Fmoc-Cys(Trt)Glu(OtBu)-Leu-OtBu
                                          (SEQ_NO 2)
Fmoc-Gly-Cys(Trt)Glu(OtBu)-

Leu-OtBu
                                          (SEQ_NO 3)
Fmoc-Asp(OtBu)-Gly-Cys(Trt)Glu(OtBu)-

Leu-OtBu
                                          (SEQ_NO 4)
Fmoc-Met-Asp(OtBu)-Gly-Cys(Trt)Glu(OtBu)-

Leu-OtBu
                                          (SEQ_NO 5)
For-Met-Asp(OtBu)-Gly-Cys(Trt)Glu(OtBu)-

Leu-OtBu

Cys-Glu-Leu
                                          (SEQ_NO 6)
Gly-Cys-Glu-Leu
                                          (SEQ_NO 7)
Asp-Gly-Cys-Glu-Leu
                                          (SEQ_NO 8)
Met-Asp-Gly-Cys-Glu-Leu
```

EXPERIMENTAL

Example 1 tripeptide INTM-2, Fmoc-Cys(Trt)Glu(OtBu)-Leu-OtBu, STEP 1+2

50 gr t-butyl Leucinate.HCl was coupled under $N_2$ with 175 gr (2.0 eq) Fmoc-Glu-(OtBu) in a solvent mixture of 2025 ml dichloromethane (27 vol) and 225 ml THF (3 vol) in the presence of EDAC, HCl (2.0 eq), and HOBt (2.0 eq) and DIPEA (5.0 eq) at initially 0-5° C. for 1 hr followed by 15-20° C. for 1 hr afforded dipeptide INTM-1, Fmoc-Glu-(OtBu)-Leu-OtBu. Identity was confirmed by $^1$H NMR and mass spectometry. For reaction with Fmoc-Cys(Trt)-OH in the next step, product isolation was omitted and the dichloromethane solution used directly after aqueous workup. The subsequent reaction of obtained dipeptide INTM-1 Fmoc-Glu-(OtBu)-Leu-OtBu was thus performed using the dichloromethane solution referred to above. Fmoc deprotection was achieved with DBU and coupling with 204 gr (1.1 eq) Fmoc-Cys(Trt)-OH in the presence of EDAC, HCl (2.0 eq), HOBt (2.0 eq) and DIPEA (4 eq) afforded the crude tripeptide INTM-2, which was purified by chromatography over silica gel (100-200) using EtOAc-hexane as eluent to furnish the tripeptide INTM-2 Fmoc-Cys(Trt)Glu(OtBu)-Leu-OtBu as an off-white color solid (148 gr, 68% overall yield over two coupling reactions, purity 93.8% by HPLC).

The above telescoped reactions STEP 1+2 were repeated from 75 gr 1-butyl Leucinate.HCl to furnish 208 gr INTM-2.

Example 2—tetrapeptide Fmoc-Gly-Cys(Trt)Glu(OtBu)-Leu-OtBu, STEP 3

INTM-2 (Fmoc-Cys(Trt)Glu(OtBu)-Leu-OtBu) as obtained hereinabove was reacted with DBU in DCM (50 vol) to achieve Fmoc deprotection, and subsequently reacted with 1.3 eq. Fmoc-Gly-OH in the presence of DIPEA (3 eq), EDC.HCl (2.0 eq), and HOBt (2.0 eq) to afford protected tetrapeptide INTM-3 Fmoc-Gly-Cys(Trt)-Glu(OtBu)-Leu-OtBu (SEQ_NO 2). Good conversion was observed by TLC, and the DCM layer was washed with water and brine. The final organic layer was concentrated to 10-15 vol and used as such in the next stage without isolation.

Example 3—pentapeptide Fmoc-Asp(OtBu)-Gly-Cys(Trt)Glu(OtBu)-Leu-OtBu, STEP 4

Key intermediate INTM-3 Fmoc-Gly-Cys(Trt)-Glu(OtBu)-Leu-OtBu as obtained hereinabove as a concentrated DCM solution was first reacted with DBU to achieve Fmoc deprotection. Before proceeding with the next coupling step, the reaction mass was passed through a silica plug to remove DBU, which has been found in previous experiments to induce formation of an undesired aspartimide by-product. Removal of DBU before coupling with Fmoc-Asp-OtBu effectively suppresses the aspartimide formation. After silica plug treatment the DCM solution was reacted with Fmoc-Asp(OtBu) in the presence of DIPEA, EDAC, HCl (1.2 eq), and HOBt (1.2 eq) to afford protected pentapeptide INTM-4 Fmoc-Asp(OtBu)-Gly-Cys(Trt)-Glu(OtBu)-Leu-OtBu (SEQ_NO 3). Product identity was confirmed by by $^1$H NMR and mass spectometry.

The telescoped reactions (STEP 3+STEP 4) were repeated twice starting from 148 gr and 190 gr INTM-2, affording 107 and 178 gr INTM-4 respectively (58.1% and 75.4% of theory).

Example 4—hexapeptide Fmoc-Met-Asp(OtBu)-Gly-Cys(Trt)-Glu(OtBu)-Leu-OtBu, STEP 5

Fmoc deprotection of the obtained pentapeptide INTM-4 from Example 3 was achieved with DBU, and coupling with Fmoc-Met in DCM-THF (50 vol+10 vol) as solvent in the presence of DIPEA (3.0 eq), EDC.HCl (2.0 eq), and HOBt.H$_2$O (2.0 eq) afforded the protected Foxy-5 derivative INTM-5 Fmoc-Met-Asp(OtBu)-Gly-Cys(Trt)-Glu(OtBu)-Leu-OtBu (SEQ_NO 4) in crude form. Purification was performed by column chromatography using DCM/THF as eluent. The purified product was slurried in DIPE to afford a white colored solid.

The purification was performed several times under various conditions, such as precipitation with anti-solvents and chromatography. The best solution was found to be column chromatography followed by slurrying in DIPE, which on 25 gr scale gave yields of 78% and 95.4% chemical purity. The reaction was repeated on 80 gr scale to provide 74 gr product (83% yield) with a chemical purity of 94.1%.

Example 5—hexapeptide INTM-6, For-Met-Asp(OtBu)-Gly-Cys(Trt)-Glu(OtBu)-Leu-OtBu, STEP 6

Fmoc deprotection of the obtained hexapeptide INTM-5 from Example 4 was achieved with DBU in DCM (50 vol) followed by coupling with formic acid (3.0 eq) in the presence of EDC.HCl (4.0 eq), HOBt.H$_2$O (4.0 eq) and DIPEA (4.0 eq) to yield INTM-6 For-Met-Asp(OtBu)-Gly-Cys(Trt)-Glu(OtBu)-Leu-OtBu (SEQ_ID NO 5).

The reaction (STEP 6) was performed three times from 4, 18 and 18 gr INTM-5, respectively, to afford yields of 75-83% and chemical purities of between 67.5-77.2%. The reaction was repeated with 10 eq Formic acid on 30 gr scale to afford 17 gr product (67% yield) with a chemical purity of 88.8%.

Example 6—hexapeptide For-Met-Asp-Gly-Cys-Glu-Leu-OH (Foxy-5), STEP 7

17 gr of the obtained hexapeptide from Example 5 was globally deprotected (Trt and tBu groups) by dissolution under N$_2$ and stirring in a cocktail of TFA (10 vol)/(i-Pr)$_3$SiH (TIS, 1.7 vol)/DTT (1.7 eq) for 15-30 min at 10-15° C. The reaction mixture was next warmed to 25 to 30° C. and stirred for 1 to 2 hrs at this temperature. The reaction mass was then concentrated under reduced pressure to 2 to 3 volumes. After completion of reaction, THF (5 vol) was added and stirring was continued for another 10-15 min at 25-30° C. Then MTBE (30 vol) was slowly added to precipitate the crude product, which was obtained as a solid in quantitative yield (12.3 gr).

The crude product was finally purified by reverse phase chromatography, which afforded the desired hexapeptide For-Met-Asp-Gly-Cys-Glu-Leu-OH (Foxy-5) in 98.3% purity using the following method conditions:
  Media: Luna C18 (3) (Make: Phenomenex) Pore Size: 10 μm
  Column id: 50 mm ID×250 mm (Novasep), Flow rate: 50.0 mL/minute.
  Sample preparation: 100 g sample dissolved in 4 mL diluent, filtered through 0.45 μm filter.
Buffer Preparation:
  Buffer-A: Prepare 0.10±0.01% Trifluoroacetic acid buffer in water by mixing 10 mL of Trifluoroacetic acid into 10 L Purified water.
  Buffer-B: Prepare 0.10±0.01% Trifluoroacetic acid buffer in Acetonitrile by mixing 5 mL of Trifluoroacetic acid into 5 L Acetonitrile.
Operational Procedure:
  1. Equilibrate the column with [Buffer A: Buffer B] in the ratio (95:5) for 3-5 column volumes with a flow rate 5.0 mL/min.
  2. Load the sample solution onto the column.
  3. Program the chromatography system hooked up to the column to deliver a gradient program as follows to start the product elution.

| Time (mins) | Flow rate (mL/minute) | Buffer-A | Buffer-B | UV Wavelength(nm) |
|---|---|---|---|---|
| 0 | 50 | 95 | 5 | 210 |
| 5 | 50 | 95 | 5 | 210 |
| 90 | 50 | 65 | 35 | 210 |

4. Collect the following fractions: Front, apex and trailing
  Note: Elution time may vary run to run due to scale dependency.
  5. After peak elution immediately wash the column with water and acetonitrile in the ratio 20:80 (% v/v) for 2 Column Volumes.
  6. Send the fractions for purity analysis.
  7. Store the fractions at −20° C.±2° C.

The invention claimed is:

1. A hexapeptide derivative of the formula:

```
PG-Met-Asp(OtBO-Gly-Cys(Trt)-
    Glu(OtBO-Leu-OR,
``` wherein R is a $C_1$-$C_6$ alkyl and PG is Fmoc.

2. A hexapeptide derivative according to claim 1 having the formula:

```
                                        (SEQ_NO 4)
Fmoc-Met-Asp(OtBu)-Gly-Cys(Trt)-
    Glu(OtBu)-Leu-OtBu.
```

3. The hexapeptide according to claim 1, wherein R is methyl or t-butyl.

4. A method for the preparation of the hexapeptide derivative according to claim 1, comprising the following steps:
   a. providing a protected L-leucine derivative PG-Leu-OR,
   b. removing the protecting group PG from said protected L-leucine derivative followed by coupling with PG-Glu-OtBu to produce a protected dipeptide PG-Glu(OtBu)-Leu-OR,
   c. removing the protecting group PG from said protected dipeptide followed by coupling with PG-Cys(Trt)-OH to produce a protected tripeptide PG-Cys(Trt)-Glu(OtBu)-Leu-OR,
   d. removing the protecting group PG from said protected tripeptide followed by coupling with PG-Gly-OH to produce a protected tetrapeptide PG-Gly-Cys(Trt)-Glu(OtBu)-Leu-OR,
   e. removing the protecting group PG from said protected tetrapeptide under basic conditions, followed by removing excess base, to produce a deblocked tetrapeptide H-Gly-Cys (Trt)-Glu(OtBu)-Leu-OR,
   f. coupling said deblocked tetrapeptide with PG-Asp (OtBu) under basic conditions, followed by removing excess base, to produce a protected pentapeptide PG-Asp (OtBu)-Gly-Cys(Trt)-Glu(OtBu)-Leu-OR,
   g. removing the protecting group PG from said deblocked pentapeptide followed by coupling with formic acid or an active ester thereof to produce the protected hexapeptide PG-Met-Asp(OtBu)-Gly-Cys(Trt)-Glu(OtBu)-Leu-OR, wherein R is a $C_1$-$C_6$ alkyl and PG is Fmoc.

5. The method according to claim 4, wherein R is methyl or t-butyl.

6. The method according to claim 4, wherein all steps b)-g) are performed in solution.

7. The method according to claim 4, wherein an intermediate purification is performed at least once between two consecutive coupling steps.

8. The method according to claim 7, wherein the intermediate purification is by flash chromatography.

9. A method for preparing Foxy-5 (SEQ_NO 1), the method comprising:
   a. providing a hexapeptide derivative according to claim 1,
   b. removing the nitrogen protecting group on the Met-terminal from said hexapeptide derivative,
   c. coupling the obtained hexapeptide of step b) with Formic acid or an active ester thereof, to produce a protected Foxy-5 derivative, For-Met-Asp(OtBu)-Gly-Cys(Trt)-Glu(OtBu)-Leu-OR,
   d. globally deprotecting the obtained protected Foxy-5 derivative of step c) to produce Foxy-5 in crude form,
   e. performing additional purification steps, and
   f. producing Foxy-5 in solid form.

10. The method according to claim 9, wherein an intermediate purification is performed at least once between two consecutive reaction steps.

11. The method according to claim 9, wherein Foxy-5 in crude form is purified by chromatography.

12. The method according to claim 9, wherein Foxy-5 is isolated in solid form as the hexapeptide or as an acidic or alkaline addition salt thereof.

13. The method according to claim 9, wherein the solid form of Foxy-5 is a lyophilisate, an amorphous powder or a crystalline compound.

14. The method according to claim 10, wherein the intermediate purification is by flash chromatography.

15. The method according to claim 11, wherein the chromatography is reverse phase chromatography.

* * * * *